United States Patent [19]
Jacobs, Jr. et al.

[11] Patent Number: 5,972,700
[45] Date of Patent: Oct. 26, 1999

[54] TM4 CONDITIONAL SHUTTLE PHASMIDS AND USES THEREOF

[75] Inventors: William R. Jacobs, Jr., City Island; Stoyan Bardarov, Bronx, both of N.Y.; Graham F. Hatfull, Pittsburgh, Pa.

[73] Assignees: Albert Einstein College of Medicine of Yeshiva University, Bronx, N.Y.; University of Pittsburgh, Pittsburgh, Pa.

[21] Appl. No.: 08/938,059

[22] Filed: Sep. 26, 1997

[51] Int. Cl.⁶ .................................................... C12N 15/63
[52] U.S. Cl. .................... 435/320.1; 435/440; 435/471; 435/473; 435/474
[58] Field of Search ............................. 435/320.1, 172.3, 435/69.1, 440, 471, 473, 474

[56] References Cited

U.S. PATENT DOCUMENTS 5,504,005  4/1996  Bloom et al. ........................ 435/253.1

FOREIGN PATENT DOCUMENTS

88/06626  9/1988  WIPO .

OTHER PUBLICATIONS

Seres et al. Zbl. Bakt. vol. 275, pp. 54–62, 1991.

MsAdam et al. Infection and Immunity, vol. 63, No. 3, pp. 1004–1012, Mar. 1995.

Kleckner et al. in Methods in Enzymology, vol. 204, pp. 139–142 and 157–160, 1991.

*Primary Examiner*—James Ketter
*Assistant Examiner*—Irem Yucel
*Attorney, Agent, or Firm*—Amster, Rothstein & Ebenstein

[57] ABSTRACT

The present invention provides a conditional shuttle phasmid constructed by inserting a cosmid into a non-essential region of the TM4 mycobacteriophage that introduces DNA of interest into mycobacteria, especially *M. tuberculosis* complex organisms and other slow growing mycobacteria. The present invention provides a recombinant mycobacterium which expresses a DNA of interest incorporated into its chromosome by a TM4 conditional shuttle phasmid containing the DNA of interest. The present invention further provides a mycobacterial auxotrophic mutant and a method of generating auxotrophic mutants.

10 Claims, 3 Drawing Sheets

SEQUENCE LISTING

```
<160> NUMBER OF SEQ ID NOS: 2

<210> SEQ ID NO 1
<211> LENGTH: 21
<212> TYPE: DNA
<213> ORGANISM: Mycobacteria

<400> SEQUENCE: 1
ggcgtaggaa cctccatcat c                                       21

<210> SEQ ID NO 2
<211> LENGTH: 22
<212> TYPE: DNA
<213> ORGANISM: Mycobacteria

<400> SEQUENCE: 2
cttgctcttc cgcttcttct cc                                      22
```

TM4 CONDITIONAL SHUTTLE PHASMIDS AND USES THEREOF

STATEMENT OF GOVERNMENT INTEREST

This invention was made with government support under NIH Grant Nos. AI26170, AI27235, and AI23545. As such, the government has certain rights in this invention.

BACKGROUND OF THE INVENTION

In April 1993 tuberculosis was declared as a global health emergency—the first such designation in the history of the World Health Organization. The distinction is regrettably justified because tuberculosis remains one of the largest burdens of disease and death in the world (Murray, C., et al. (1990) Bull. Int. Union Tuberc. Lung Disorders 65, 6–26; Murray, C., et al. (1997) in Global Burden of Diseases (Harvard Univ. Press, Cambridge, Mass.) p. 273) due in part to the increased susceptibility of HIV infected individuals and the ominous emergence of multi-drug resistant strains in both industrialized and developing countries. Effective new tuberculosis control and prevention strategies will require additional knowledge of the causative agent and its interaction with the human host. To systematically delineate virulence determinants, identify the metabolic pathways and discover novel drug targets for M. tuberculosis, a methodology generating libraries of mutants will be essential. Although mutant isolation and gene transfer strategies have been successfully employed for fast-growing non-virulent mycobacteria, such as M. smegmatis (Tokunaga, T., Mizuguchi, Y., & Suga, K. (1973) J. Bacteriol. 113, 1104–1111; Sudaraj, C. V. & Ramakrishnan, T. (1971) Nature (London) 228, 280–281), determining the genetic basis of phenotypes for M. tuberculosis has been frustrated by the lack of a natural gene transfer system in this pathogen. Furthermore, traditional mutational analyses based on the characterization of colonies arising from single cells following treatment with DNA damaging agents is of limited value for slow-growing mycobacteria, since the frequency of mutants is very low, multiple mutations occur in the same cells, and the mycobacteria tend to clump. Also, since M. tuberculosis or BCG have slow generation times (20 h–24 h), three to four weeks are required to visualize colonies arising from single cells, and many mutants are likely to grow even more slowly.

Transposon mutagenesis has been successfully used in diverse genera of bacteria (Berg, C. M., et al. (1989) In: Mobile DNA. American Society of Microbiology, Washington D.C. pp. 879–925). The first transposition events in M. smegmatis were reported using Tn610(Martin, C., et al. (1990) Nature (London) 21, 739–743), followed by transposons engineered from insertion elements IS900 and IS986 (Fomukong, N. G. & Dale, J. W. (1993) Gene 130, 99–105; England, P. M., Wall, Q., & McFadden, J. (1991) Mol. Microbiol. 5, 2047–2052). Transposition in BCG (McAdam, R.A., (1995) Infect. Immunol. 63 1004–1012) was reported using a transposon constructed from the insertion element IS1096 (Cirillo, J. D., et al. (1991) J. Bacteriol. 173, 7772–7780). Remarkably, the only reports of successful isolation of auxotrophic mutants for mycobacteria of the M. tuberculosis group have employed the use of insertional mutagenesis systems: illegitimate recombination (Kalpana, V. G., et al. (1991) Proc. Natl. Acad. Sci. USA 88, 5433–5437), transposon mutagenesis (M$^c$Adam, R. A., et al., (1995) Infect. Immun. 63, 1004–1012), and allelic exchange (Balasubramanian, V., et al. (1996) J. Bacteriol. 178, 273–279). A very promising approach to deliver transposons into M. smegmatis is the use of a conditionally replicating vector which is able to replicate at 30° C., but not at 37° C. (Guilhot, C., et al. (1994) J. Bacteriol. 176, 535–539). A library of 30,000 Tn611 insertion mutants was obtained from three independent experiments yielding 80 auxotrophic mutants with 15 different phenotypes. However, this system had not yet been applied to the slow-growing mycobacteria such as M. tuberculosis.

Conditionally replicating phage systems have proven to be very efficient systems for transposon mutagenesis in numerous bacterial species (Kleckner, N., et al. (1991) Methods Enzymol. 204 139–180). One of the great advantages of a phage delivery system is that essentially every cell in the bacterial population can be infected with the transposon-carrying phage, generating large numbers of independent mutants. Shuttle phasmid vectors, chimeric molecules that replicate in E. coli as plasmids and in mycobacteria as phages, were the first recombinant DNA vectors engineered for mycobacteria (Jacobs, Jr., W. R., Tuckman, M., & Bloom, B. R. (1987) Nature (London) 327, 532–536). Various phasmids, constructed from different mycobacteriophages, such as TM4, L1, and D29, have proven useful for the development of transformation systems for mycobacteria (Snapper, S. B., (1988) Proc. Natl. Acad. Sci. USA 85, 6987–6991) and the development of luciferase reporter phages for rapid diagnosis and drug susceptibility testing of M. tuberculosis clinical isolates (Jacobs, W. R., et al. (1993) Science 260, 819–822; Pearson, R. E., et al. (1996) Gene 183, 129–136).

Because the creation of mutants in M. tuberculosis and BCG is of essential importance in the analysis of gene function, it is desirable to develop effective means and methods for delivering foreign DNA into M. tuberculosis and BCG. The insertion of foreign DNA into M. tuberculosis and BCG mycobacteria would provide the necessary tools for understanding the mechanisms by which these mycobacteria survive and replicate. In addition, it would provide valuable tools for the development of vaccines and new drugs effective in the treatment of infection caused by M. tuberculosis and BCG.

SUMMARY OF THE INVENTION

The present invention provides a TM4 shuttle phasmid capable of introducing DNA of interest into a mycobacterium. Further provided by the present invention is a conditional TM4 shuttle phasmid capable of introducing DNA of interest into a mycobacterium.

The present invention also provides a conditional shuttle phasmid that contains DNA of interest inserted into the phasmid.

The present invention further provides a recombinant mycobacterium which expresses DNA of interest introduced into a chromosome of the mycobacterium by a conditional shuttle phasmid containing the DNA of interest.

The present invention also provides an auxotrophic mutant produced by infecting a mycobacterium with a conditional shuttle phasmid containing a transposon such that the transposon incorporates randomly into a chromosome of the mycobacterium.

Finally, the present invention provides a method for producing a mutant mycobacterium comprising infecting the mycobacterium with a TM4 conditional shuttle phasmid containing a transposon wherein the infection takes place under non-permissive wherein said conditional shuttle phasmid does not replicate and said transposon contained in said conditional shuttle phasmid incorporates into a chromosome of said mycobacterium, thereby generating one or more mutations in said mycobacterium.

Additional objects of the present invention will be apparent from the description which follows.

BRIEF DESCRIPTION OF THE FIGURES

FIG. 1.

FIGS. 2A–2C: FIGS. 2A–2C sets forth the results of a Southern blot analysis of transposon mutants. FIGS. 2B and 2C show Southern Blot Analysis of IS1096 in fast-growing mycobacteria. FIG. 2B shows the chromosomal DNAs hybridized with tnpA of IS1096.

FIG. 3: FIG. 3 depicts the distribution of Tn5367 insertions on the genome map of *M. tuberculosis*. The location of the Tn5367 insertions in mutants generated from *M. tuberculosis* Erdman (mc$^2$ 3000's) or BCG (mc$^2$ 1500's) were deduced from the determination of the sequence adjacent to the insertion and comparison to the *M. tuberculosis* genomic database and the *M. tuberculosis* physical map (Pearson, et al. (1996) *Gene* 183, 129–136).

DETAILED DESCRIPTION OF THE INVENTION

The present invention provides a novel class of conditional shuttle phasmids based on the TM4 mycobacteriophage for introducing DNA of interest into mycobacteria. As used herein, "conditional" shuttle phasmids are those which replicate only under certain conditions, such as a specific temperature. The cloning vectors of the present invention are particularly suited for introducing DNA of interest into *Mycobacterium tuberculosis* complex organisms, i.e., *M. tuberculosis, M. bovis, M. phlei* and Bacille-Calmette-Geurin (BCG), and other slow growing mycobacteria as well as nontuberculosis mycobacteria commonly encountered in biological samples isolated from human subjects, e.g., *M. avium-intracellulare, M. kansasii, M. xenopi, M. scrofulaceum, M. simiae, M. szulgai, M. gordonae, M. gastri, M. smegmatis,* and *M. chelonae.*

The conditional shuttle phasmids of the present invention are produced by inserting a cosmid into a non-essential region of the TM4 genome. DNA of interest may be inserted in the cosmid, and the conditional shuttle phasmids containing the DNA of interest may be used to infect mycobacteria and introduce the DNA of interest into the chromosome of a mycobacterium by homologous recombination, site-specific recombination or nonhomologous recombination. The DNA of interest may be of any origin and may encode proteins or polypeptides of interest including but not limited to antigens, anti-tumor agents, enzymes, lymphokines, pharmacologic agents, immunopotentiators, and reporter molecules of interest.

Antigens include but are not limited to *Mycobacterium leprae* antigens; *M.tuberculosis* antigens; Rickettsea antigens; malaria sporozites and meroziotes; diptherea toxiods; tetanus toxoids; Clostridium antigens; Leishmania antigens; Salmonella antigens; Borrelia antigens; *M. africanum* antigens; *M.intracellulare* antigens; *M.avium* antigens; Treponema antigens; Pertussis antigens; Schistosoma antigens; Filaria antigens; Herpes virus antigens; influenza and parainfluenza virus antigens; measles virus antigens; mumps virus antigens; hepatitis virus antigens; rabies virus antigens; Shigella antigens; Neisseria antigens; polio virus antigens; Rift Valley Fever virus antigens; dengue virus antigens; Human Immunodeficiency Virus (HIV) antigens; respitory syncytial virus (RSV) antigens; snake venom antigens; and *Vibrio cholera* antigens. Enzymes which may be encoded include, but are not limited to, steroid enzymes.

Anti-tumor agents which may be encoded include, but are not limited to, interferon-alpha, interferon-beta, or interferon-gamma, and tumor necrosis factor (TNF). Lymphokines which may be encoded include but are not limited to interleukins 1 through 8. Reporter molecules include, but are not limited to, luciferase (from Vibrio or from firefly), beta-galactosidase, beta-glucuronidase, and catechol dehydrogenase. Other peptides or proteins which may be encoded by the DNA of interest include, but are not limited to, stress proteins, which can be administered to evoke an immune response or to induce tolerance in an autoimmune disease, e.g., rheumatoid arthritis.

The conditional shuttle phasmid of the present invention may also be used to introduce transposons into the chromosome of a mycobacterium. As used herein, the term "transposon" is a general term which encompasses both non-mutated transposons and mutated transposons, i.e., a transposon in which a portion of the nucleotide sequence has been deleted and/or replaced, and/or wherein the transposon contains additional DNA sequences. In general a transposon contains an inverted repeat sequence at the 5' and 3' end, and a gene(s) encoding a transposase enzyme(s) between the inverted repeat sequences. The transposase(s) acts upon the inverted repeat sequences so as to enable the transposon to remove itself from the shuttle phasmid and insert or transpose into the chromosome of the mycobacteria. In some instances, the transposon may also include gene(s) encoding resolvase(s) and/or regulatory protein(s) which regulate transposition.

In one embodiment of the invention, a conditional shuttle phasmid that contains an *E. coli* bacteriophage lambda cosmid inserted in a non-essential region of the TM4 mycobacteriophage. This conditional shuttle phasmid, designated phAE87, was deposited under the terms of the Budapest Treaty on Sep. 26, 1997 with the American Type Culture Collection (ATCC), 10801 University Blvd., Manassas, Va. 20110-2209, and assigned ATCC Accession No. 209306.

In another embodiment of the invention, a conditional shuttle phasmid contains the TN5367 transposon inserted into an E. coli bacteriophage lambda cosmid inserted in a non-essential region of the TM4 mycobacteriophage. This conditional shuttle phasmid, designated phAE94, was deposited under the terms of the Budapest Treaty on Sep. 26, 1997 with the American Type Culture Collection (ATCC), 10801 University Blvd., Manassas, Va. 20110-2209, and assigned ATCC Accession No. 209307.

DNA of interest may be obtained from by a variety of methods, e.g., DNA may be isolated directly from an organism using standard purification procedures or by the cloning and amplification of the DNA of interest using methods known to one skilled in the art of genetic engineering such as PCR. Cloning of the DNA of interest into the conditional shuttle phasmid of the present invention may be accomplished using standard cloning and DNA ligation techniques. For example, the cohesive ends of the shuttle phasmid may be ligated using known ligase enzymes and the resulting molecule digested with a unique restriction endonuclease. Alternatively, a polylinker sequence containing recognition sites for a number of unique restriction enzymes may be inserted into the shuttle phasmid and the polylinker sequences digested with one or more restriction endonucleases in order to generate appropriate restriction sites on the shuttle phasmid to facilitate insertion of the DNA of interest. The use of two unique restriction endonucleases may be preferred for the directional cloning of the DNA of interest.

In addition to the DNA of interest, a selectable marker gene, e.g. a gene which confers antibiotic resistance, may be ligated to the DNA of interest and the resultant molecule ligated into the conditional shuttle phasmid using standard procedures (the conditional shuttle phasmid generally contains antibiotic resistance genes for selection of colonies in E. coli). Selectable marker genes which may be included on the DNA of interest are well known in the art and include but are not limited to genes encoding resistance to viomycin, thiostrepton, tetracycline, hygromycin or bleomycin. In a preferred embodiment of the invention, the selectable marker gene included on the DNA of interest is a gene encoding kanamycin resistance.

The resulting ligated DNA comprising conditional shuttle phasmid DNA, DNA of interest and/or selectable marker DNA is then packaged into bacteriophage lambda heads using a commercially available in vitro packaging mix. E. coli is subsequently transduced with the phage colonies containing the ligated DNA and are isolated by virtue of their ability to grow in medium containing the antibiotic corresponding to the resistance gene on the cosmid.

The resulting shuttle phasmids are introduced into M. smegmatis or other suitable mycobacteria using standard methods known to those skilled in the art, such as electroporation. Plaques which contain shuttle phasmids comprising the DNA of interest may be used to infect mycobacteria of interest, e.g., M. tuberculosis and BCG.

Infection of mycobacteria such as M. tuberculosis with conditional shuttle phasmids containing the DNA of interest is accomplished by mixing the mycobacteria and shuttle phasmid at the non-permissive temperature at a multiplicity which will insure infection of mycobacterium. As used herein, a "non-permissive" temperature is the temperature at which the conditional shuttle phasmid will not replicate. The calculation of the correct multiplicity is well within the knowledge of one skilled in the art. The phasmid DNA thus enters the mycobacterium but is unable to replicate. In this way the DNA of interest can become integrated into the mycobacterial chromosome and so expressed. Selection of mycobacteria containing the DNA of interest can be detected by virtue of their survival and growth on medium containing the antibiotic corresponding to the selectable markers encoded by the DNA of interest. Alternatively, mycobacteria expressing antigens or other proteins may also be detected by other methods, e.g., use of monoclonal antibodies.

The present invention also provides a method for producing a mutant mycobacterium comprising infecting the mycobacterium with a TM4 conditional shuttle phasmid containing a transposon wherein the infection takes place under non-permissive wherein said conditional shuttle phasmid does not replicate and said transposon contained in said conditional shuttle phasmid incorporates into a chromosome of said mycobacterium, thereby generating one or more mutations in said mycobacterium. The conditional shuttle phasmids of the present invention may be used to produce a mutated mycobacterium, and to generate libraries of mutated mycobacteria, using conditional shuttle phasmids containing transposons such as Tn5367 and mini-Tn10(kan). The mutated mycobacterium, or the library of mutated mycobacteria, may be generated in mycobacteria such as, for example, M. phlei, M. tuberculosis and BCG. Transposition of the mycobacterium or mycobacterial library may occur randomly or site-specifically. The transpositions may occur in any or every quadrant of the mycobacterial genome. As used herein, a mycobacterial "genome" is one haploid set of mycobacterial chromosomes with the genes they contain.

The conditional shuttle phasmids of the present invention may also be used to produce a mutated mycobacterium, or to generate libraries of mutated mycobacteria, using conditional shuttle phasmids containing DNA of interest, the expression of which will inactivate a specific mycobacterial gene or genes, e.g., antisense RNA.

The conditional shuttle phasmids of the present invention can be conditionally replicating vectors by virtue of: (1) a thermogenic mutation in a phage gene; (2) the phage contains an amber mutation in the phage gene in an M. smegmatic containing an amber supressor tRNA gene; (3) a phage with a deleted gene in a M. smegmatis containing the gene that is deleted expressed from an exogneous promoter in the M. smegmatis.

Such methods are able to produce auxotrophic mutants, i.e., mutants which require a nutrient or substance not required by the organism from which the mutant was derived, e.g. leucine and other amino acids. Such non-pathogenic mycobacteria may be produced by insertional mutations or deletions causing disruptions of a mycobacterial virulence gene or by the expression of a molecule to block expression of the virulence gene, e.g. by knocking out genes in the mycobacteria which encode virulence factors, enzymes involved in regulation of pathways of the mycobacterium, and the like. Thus the conditional shuttle phasmid of the present invention may be used to generate a library of *M. tuberculosis* mutants that can be screened for their utility as vaccine strains.

The present invention also relates to methods of vaccinating a host with the recombinant mycobacterium to elicit protective immunity in the host. The recombinant vaccine can be used to produce humoral antibody immunity, cellular immunity (including helper or cytoxic immunity) and/or mucosal or secretory immunity. In addition, the present invention relates to the use of the antigens expressed by the recombinant cultivable mycobacterium as vaccines or diagnostic reagents as described in WO 90/00594, which is incorporated by reference in its entirety.

Mycobacteria are well known adjuvant properties and so are able to stimulate a subject's immune response to respond to other antigens with great effectiveness. Their adjuvant properties are especially useful in providing immunity against pathogens in cases where cell mediated immunity is critical for resistance. In addition, the mycobacterium stimulates long-term memory or immunity thus a single inoculum may be used to produce long-term sensitization to protein antigens. The mycobacterial vaccine of the present invention may be used to prime long-lasting T cell memory, which stimulates secondary antibody responses which will neutralize infectious agents or toxins, e.g., tetanus and diptherea toxins, pertussis, malaria, influenza, herpes viruses and snake venoms.

BCG is an especially appropriate vaccine vehicle in that it is the only childhood vaccine currently given at birth, it has a low incidence of adverse effects when given as a vaccine against tuberculosis and it can be used repeatedly in an individual. A further advantage of BCG and mycobacteria in general is the large size of their genomes (approximately $3\times10^6$ bp). The large size enables DNA from other sources to be stably incorporated thus making multi-vaccine possible, i.e., a mycobacterium which expresses DNA of interest which encodes antigens from more than one pathogen.

The conditional shuttle phasmids are useful for the transient delivery of genes encoding γδ-resolvase or Cre recombinase to mycobacteria for precise gene deletions and removal of selective markers for creating non-reverting, attenuated vaccine strains acceptable for use in humans.

The vaccines or therapeutic agents containing transformed mutated mycobacteria are administered in conjunction with a suitable pharmaceutical carrier. Mineral oil, alum, synthetic polymers are representative examples of suitable carriers. Vehicles for vaccines and therapeutic agents are well known in the art and the selection of a suitable vehicle is well within the skill of one skilled in the art. The selection of a suitable vehicle is also dependent upon the manner in which the vaccine or therapeutic agent is to be administered. The vaccine or therapeutic agent may be in the form of an injectable dose and may be administered intramuscularly, intravenously, orally, intradermally, or by subcutaneous administration.

The conditional shuttle phasmids of the present invention can also be used in the diagnosis of infection by mycobacteria. For example, a shuttle phasmid specific for *M. tuberculosis* or other type of mycobacteria may be ligated to a reporter molecule, e.g., luciferase from Vibrio or of firefly origin; beta-galactosidase; beta-glucuronidase; or catechol dehydrogenase and a strong mycobacterial promoter which controls expression of the reporter molecule-encoding gene. A sample from a subject suspected of suffering from an infection can be tested. The sample is cultured and combined with the specific phage. After a short time, e.g., hours, under appropriate conditions, the sample is assayed using known techniques, to detect the reporter molecule encoded by the DNA in the vector. Infection of mycobacteria using the conditional shuttle phasmids of the present invention which contain the firefly luciferse gene increases the cumulative light emmission and extends the time available for the assay.

Mycobacteria can also be used as a source of a protein encoded by a DNA of interest. The DNA of interest may have a signal sequence added, e.g., from alpha antigen, which is secreted in mycobacteria, beta-galactosidase, agarase or alpha amylase in order to facilitate transport of the protein out of the mycobacterial cell.

In a preferred embodiment of the invention, TM4 conditionally-replicating shuttle phasmid vectors are produced which replicate in *M. smegmatis* at 30° C., but fail to replicate and lyse their host cells at 37° C. These phasmids are engineered to deliver transposons such as Tn5367 and mini-Tn10(kan) to efficiently generate transposon libraries of *M. phlei,* BCG and *M. tuberculosis* mutants.

The present invention is described in the following Experimental Details Section which is set forth to aid in the understanding of the invention, and should not be construed to limit in any way the scope of the invention as defined in the claims which follow thereafter.

EXPERIMENTAL DETAILS SECTION

I. Materials and Methods

Bacterial strains, media, and culture methods. The mycobacterial strains used in this study are as follows: *M. aurum,* $mc^2$18 (obtained from W. Jones, CDC); *M. chelonae* $mc^2$21 (obtained from W. Jones, CDC); *M. phlei,* $mc^2$19, phage host (obtained from W. Jones, CDC); *M. phlei,* ATCC354, NTCC54 (obtained from the ATCC); *M. phlei,* ATCC11758, TMC1548, Type strain (obtained from the ATCC); *M. phlei,* ATCC27086, Jahasz F89 (obtained from the ATCC); *M. phlei,* ATCC27206, SN109 (obtained from the ATCC); *M. fortuitum,* ATCC6841, TMC1529 (obtained from the ATCC); *M. fortuitum,* ATCC35755, TMC1545 (obtained from the ATCC); *M. flavescence,* ATCC14474, TMC1541 (obtained from the ATCC); *M. smegmatis,* $mc^2$155, ept-1 (Hendrix, R. W., et al. (1983) in "Lambda II", Cold Spring Harbor Laboratory, Cold Spring Harbor, N.Y. pp.310–311); *M. smegmatis,* $mc^2$1255, ept-1 rpsL4 (Pavelka, M. S., et al. (1996) *J. Bacteriol.* 178, 6496–6507); *M. smegmatis,* ATCC359, alias *M. butiricum* (obtained from the ATCC); *M. smegmatis,* ATCC11759, Penso strain Milch (obtained from the ATCC); *M. smegmatis,* ATCC23032, Runyon Special 9 (obtained from the ATCC); *M. smegmatis,* ATCC27204, SN2 (obtained from the ATCC); *M. smegmatis,* ATCC27205, SN38 (obtained from the ATCC); *M. smegmatis,* ATCC35797, TMC1515 (obtained from the ATCC); *M. smegmatis,* ATCC37798, TMC1533 "R. Koch" (obtained from the ATCC); *M. vaccae,* ATCC15483, TMC1526 SN920 (obtained from the ATCC); *M. vaccae*, ATCC23014, SN923 (obtained from the ATCC); BCG, Pasteur strain (obtained from Statens Serum Inst.); *M. tuberculosis*, Erdman, Virulent isolate (obtained from F. Collins, FDA).

The *E.coli* strains, DH5α or HB101, used for cloning hosts, were grown as previously described (Sambrook, J. Fritsch, E. F. & Maniatis, T. (1989) in: *"Molecular cloning: a laboratory manual"* 2 ed. Cold Spring Harbor laboratory, Cold Spring Harbor, N.Y.). For preparation of electrocompetent cells for transfections, *M. smegmatis* mc$^2$155 or mc$^2$1255 were grown in LBT broth (Pavelka, M. S., Jr. & Jacobs, W. R., Jr. (1996) *J. Bacteriol.* 178, 6496–6507). Mycobacteriophages were propagated in mc$^2$155 as described in Jacobs, W. R., Jr., et al., (1991) *Methods Enzymol.* 204, 535–555. When required, the following antibiotics were used at the specified concentrations: carbenicillin (50 μg/ml), kanamycin (25 μg/ml for *E. coli*; 20 μg/ml for mycobacteria); BCG, *M. tuberculosis* Erdman strain and other mycobacteria were grown in Middlebrook 7H9 broth enriched with albumin (fraction V) 0.5%, dextrose 0.2%, sodium chloride 0.85%, and Tween 80 0.05% (M-ADC-TW) broth (Jacobs, W. R. Jr., (1991) *Methods Enzymol.* 240, 535–555). For transposon delivery experiments, BCG and *M. tuberculosis* were grown in M-ADC-TW broth without glycerol.

Isolation of temperature-sensitive mycobacteriophages. TM4 shuttle phasmids were propagated in *M. smegmatis* mc$^2$155. Samples of phages ($10^9$ PFU/ml) were mutagenized with hydroxylamine as set forth in Davis, R. W., Botstein, D. & Roth, J. R. (1980) in: *Advanced Bacterial Genetics, CSH*, pp. 94–95, using conditions that yielded 0.1% viable surviving phages. These were plated on *M. smegmatis* mc$^2$155 and incubated for 24 hours at 30° C. until very small plaques appeared. Plates were then shifted at 42° C. and incubated for another 24 to 36 hours. Phage plaques which remained very small after this incubation period were screened for their abilities to form plaques at 30° C., 37° C., and 42° C. Phage clones forming plaques at 30° C., but not at 42° C. were clone purified, amplified to a high titer and analyzed for reversion frequency. Several rounds of mutagenesis were performed to obtain mutants that are unable to plaque at 37° C. Shuttle phasmids from PH101 were prepared as described previously (Jacobs, Jr., W. R., et al. (1987) *Nature* (London), 327, 532–536; Jacobs, Jr., W. R., et al. (1993) *Science,* 260 819–822; Pearson, R. E., et al. (1996) *Gene,* 183 129–136).

Recombinant DNA Methodologies. Cosmids, phasmids, transposons, and phages used are as follows: Transposons: Tn5367 (IS1096 derived transposon containing Kan$^r$ gene (McAdam, et al. (1995) *Infect. Immun.* 63, 1004–1012)); mini-Tn10(kan) (derivative of Tn10 containing aph gene (Kleckner, et a. (1991) *Meth. Enzymol.* 204, 139–180)). Cosmids: pYUB328 (ColE1 amp$^r$ excisable double cos vector (Balasubramanian, V., et al. (1996) *J. Bacteriol.* 178, 273–279)); pYUB552 minimal (2.4-kb pYUB328 cosmid derivative (described herein)); pYUB553 (pYUB552::Tn5367 (described herein)); pYUB554 (pYUB552::mini-Tn10(kan) (described herein)). Phages: λ (cI857, Sam10); TM4 (wild type (Jacobs, Jr., W. R., et al. (1987) *Nature* (London) 327, 532–536)); PH101 (ts mutant of TM4 that fails to form plaques at 42° C. (described herein)). Shuttle phasmid: phAE87 (PH101::pYUB328 that fails to replicate at 37° C. (described herein)). Conditionally-replicating transposon delivery shuttle phasmids: phAE94 (phAE87::pYUB553 (described herein)).

DNA manipulations were done essentially as previously described (Sambrook, J. Fritsch, E. F. & Maniatis, T.(1989) in: *"Molecular cloning: a laboratory manual"* 2 ed. Cold Spring Harbor laboratory, Cold Spring Harbor, N.Y.). High-molecular weight chromosomal DNA from BCG or *M. tuberculosis* for generating cosmid libraries was purified as described previously (Balasubramanian, V., et al. (1996) *J. Bacteriol.* 178, 273–279).

Construction of pYUB552—a minimal excisable cosmid vector. The 335 bp cos DNA sequence from bacteriophage λ necessary for in vitro packaging (Hendrix, R. W., Roberts, J. W. & Weisberg, R. A. (1983) in: *"Lambda II"*, Cold Spring Harbor Laboratory, Cold Spring Harbor, N.Y. pp. 310–311) was amplified by PCR using two sets of primers generating a ClaI-XbaI fragment and an XbaI-AsuII fragment. The PCR products were digested with XbaI, and ligated to form a double cos fragment. This product (double cos), 660 bp in length was used to replace the ClaI-AsuII double cos fragment of pYUB328, thus generating pYUB551. A single cos vector, pYUB552, was obtained by removing one of the cos sites in pYUB551 by digesting with XbaI and AsuII. Tn5367 was purified as 3022 bp restriction enzyme fragment from pYUB281 and cloned into the BspHI site of pYUB552, thus replacing the ampicillin resistance gene and generating pYUB553. Mini Tn10(kan) was isolated from pNK2859 (Kleckner, N., et al. (1991) *Meth. Enzymol.* 204 139–180) by a BamHI digestion and cloned into the BspHI site of pYUB552, replacing the ampicillin-resistance gene to generate pYUB554.

Transposon mutagenesis. Fast growing mycobacteria were cultured LBT to an OD at $A_{600}$ of 1.0 (approximately $2\times10^8$ CFU/ml). BCG and *M. tuberculosis* were grown for 7 to 10 days following inoculation of 10 ml of the starter culture into a 100-ml roller bottle culture ($A_{600}$=1.0) in M-ADC-TW without glycerol plus 0.4% casamino acids. Ten ml of cultures were concentrated by centrifugation, and resuspended in 1 ml of MP buffer (Jacobs, Jr., W. R., et al. (1991) *Meth. Enzymol.* 204 535–555). The cells were pre-warmed at the non-permissive temperature (37° C.) and were then mixed with $2\times10^{10}$ PFU/ml (MOI=10). The cell-phage mixture was incubated at the non-permissive temperature for 30 min for the fast growing mycobacteria or 4 to 6 hours for the slow growing mycobacteria. After completion of the adsorption time, 2 ml of pre-warmed "Adsorption-stop buffer" (MP buffer containing 20 mM NaCitrate and 0.2% Tween 80) was added to prevent further phage infections. Samples of this mixture were plated on pre-warmed TSA plates for the fast-growing mycobacteria or M-ADC-TW based agar media containing 0.1% Tween80, 0.4% casamino acids, 40 μg/ml L-tryptophan and 20 μg/ml kanamycin for the slow-growing mycobacteria. Transposition frequency was estimated as a number of Kan$^r$ colonies per total number of input cells.

Southern blotting and DNA sequencing. Southern blotting was done by the alkali-denaturing procedure. DNA was transferred to Biotrans nylon membranes (ICN, Irvine, Cal.)

by the capillary method. Hybridization and detection were done as recommended by the manufacturer (ECL, Amersham, United Kingdom). Sequence analysis was performed using the Applied Biosystems Prism Dye Terminator Cycle Sequencing Core kit with AmpliTaq DNA polymerase (Perkin Elmer, Norwalk, Conn.) and an Applied Biosystems 377 automated DNA sequencer. Chromosomal DNA sequence at the junction of the transposon insertions was obtained by PCR sequencing outwards from the transposon using primers HOPS1 (5'-GGCGTAGGAACCTCCATCATC-3') SEQ. ID. NO.: 1 and HOPS2 (5'-CTTGCTCTTCCGCTTCTTCTCC-3') SEQ. ID. NO.: 2 with cosmid DNA as a template. The sequence thus obtained (400 to 600 bp) was used to blast-search the *M. tuberculosis* Sanger Sequence Data base or GenBank Data Base using MacVector software (Scientific Imaging Systems, Eastman Kodac, New Haven, Conn.).

II. Results

Figure 1:
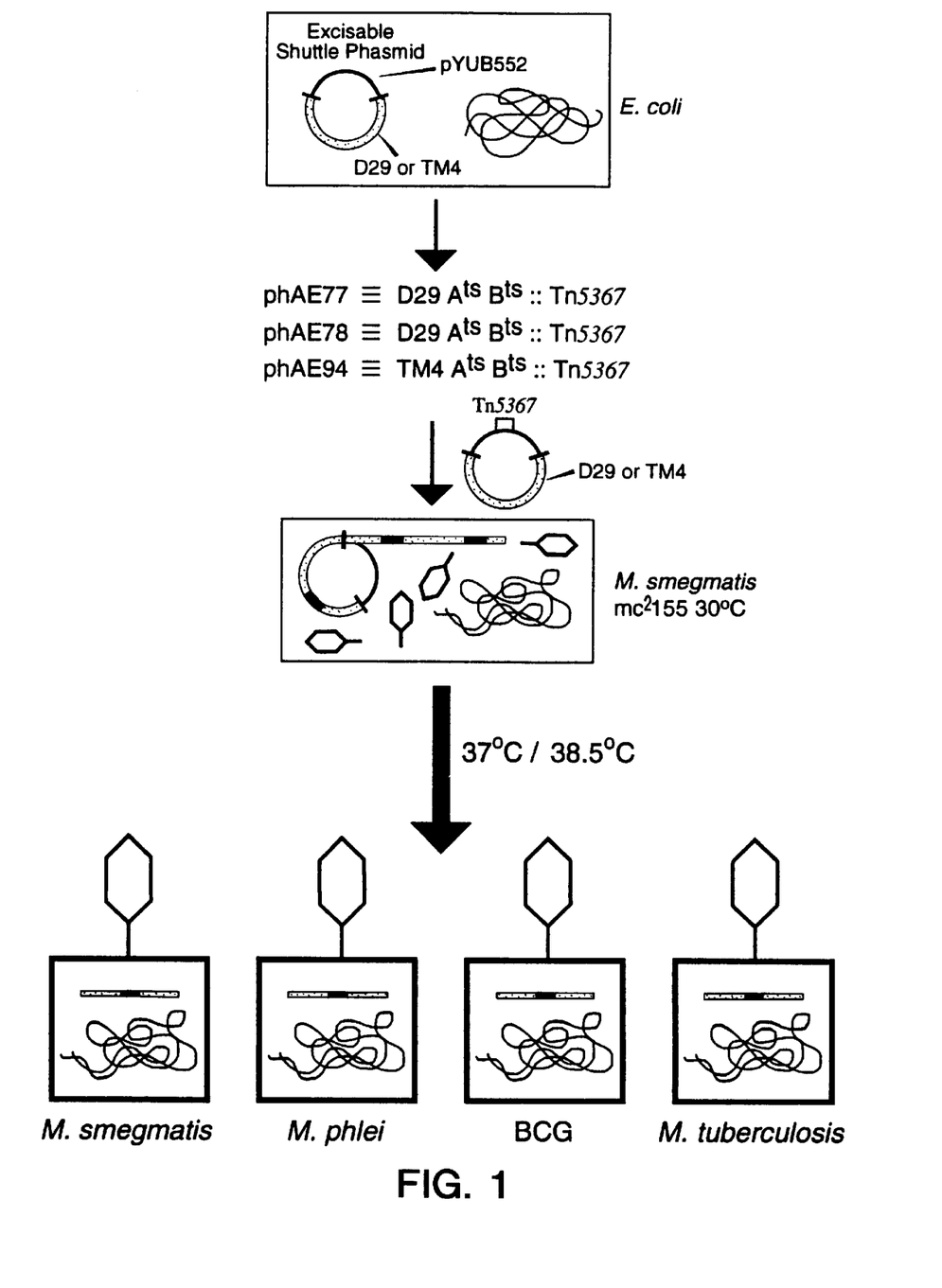
FIG. 1 sets forth a diagram of transposon delivery in mycobacteria using conditionally replicating shuttle phasmids.

Development of conditionally-replicating shuttle phasmids. Conditionally-replicating mycobacteriophage vectors may be used for the delivery of transposons to a broad range of mycobacteria including the slow growing *M. tuberculosis* and BCG (FIG. 1). Phasmid vectors with the excisable cosmid pYUB328 (Balasubramanian, V., et al. (1996) *J. Bacteriol.* 178 273–279) were chosen because these vectors provide an easy means to introduce transposons into non-essential regions of a mycobacteriophage, although other vectors may also be utilized.

Shuttle phasmids from TM4 were constructed and one such phasmid, ph101, was subjected to hydroxylamine mutagenesis. From the initial screen of 2000 mutants only phages unable to replicate at 42° C. were observed. The mutant was subjected to further mutagenesis and a set of independent mutants were identified that failed to form plaques at 37° C. The mutations conferring thermosensitive growth reverted at frequencies of less than $10^{-7}$ at 37° C. Six mutants were tested for their inability to kill *M. smegmatis* when mixed at an MOI of 10 and incubated at the non-permissive temperature, 37° C. One such mutant, phAE87, showing the lowest reversion frequency and inability to kill *M. smegmatis* when incubated at the non-permissive temperature was chosen as the TM4-based transposon delivery phage.

Delivery of transposons in fast-growing mycobacteria using conditionally-replicating shuttle phasmids. Transposon constructs could be readily introduced into phAE87 by replacing the pYUB328 cosmid with a cosmid containing the transposon of interest. To further maximize the cloning capacities, a cosmid vector, pYUB552, was engineered to contain 2.1 kb less DNA than pYUB328. Tn5367 (McAdam, R. A., et al. (1995) *Infect. Immun.* 63 1004–1012) or mini-Tn10(kan) (Kleckner, N., et al. (1991) *Meth. Enzymol.* 204 139–180) were cloned into this cosmid to generate pYUB553 and pYUB554, respectively.

TABLE 1

Transposition of Tn5367 in fast growing mycobacteria

| Genus, Species | Strain | Copies of IS1096 | Via phAE94 |
|---|---|---|---|
| *M. smegmatis* | mc$^2$155 | 11 | >10 |
| *M. smegmatis* | ATCC359 | 3 | 215 |
| *M. smegmatis* | ATCC11759 | 6 | 0 |
| *M. smegmatis* | ATCC23032 | 9 | 345 |
| *M. smegmatis* | ATCC27204 | 5 | 0 |
| *M. smegmatis* | ATCC27205 | 14 | 0 |
| *M. smegmatis* | ATCC35797 | 11 | 260 |
| *M. smegmatis* | ATCC35798 | 9 | 425 |
| *M. aurum* | mc$^2$18 | none | 0 |
| *M. chelonae* | mc$^2$21 | none | 0 |
| *M. phlei* | mc$^2$19 | none | 2000 |
| *M. phlei* | ATCC354 | none | 3 |
| *M. phlei* | ATCC11758 | none | 0 |
| *M. phlei* | ATCC27086 | none | 0 |
| *M. phlei* | ATCC27206 | none | 1 |
| *M. fortuitum* | ATCC6841 | none | 0 |
| *M. vaccae* | ATCC15483 | none | 0 |
| *M. vaccae* | ATCC23014 | none | 0 |

Tn5367 represented an attractive transposon for mutagenesis of mycobacteria, as it had been previously shown that it transposed in BCG in a relatively random fashion by a non-replicative mechanism (McAdam, R. A., et al. (1995) *Infect. Immunol.* 63 1004–1012). pYUB553 was used to replace pYUB328 into the TM4 conditionally-replicating shuttle phasmids to generate phAE94. The phAE94 vector was used to deliver Tn5367 into mc$^2$155 cells at 37° C. Very few kanamycin-resistant colonies were obtained. Southern analysis suggested that transposition had occurred, as hybridization of the kanamycin-resistant colonies with the aph gene yielded fragments of various sizes (data not shown). It is hypothesized that the low frequency of transposition of Tn5367 in mc$^2$155 might be a result of a negative-regulation resulting from the 11 copies of IS1096. Searching for an alternative fast-growing mycobacterial host, various strains were screened of *M. smegmatis, M. aurum, M. fortuitum, M. chelonei, M. phlei,* and *M. vaccae*. Transposition in three different *M. smegmatis* strains and one *M. phlei* (mc$^2$19) strain were observed, whereas no or very low frequency of transposition occurred in the others (see Table 3, below).

Figure 2A:
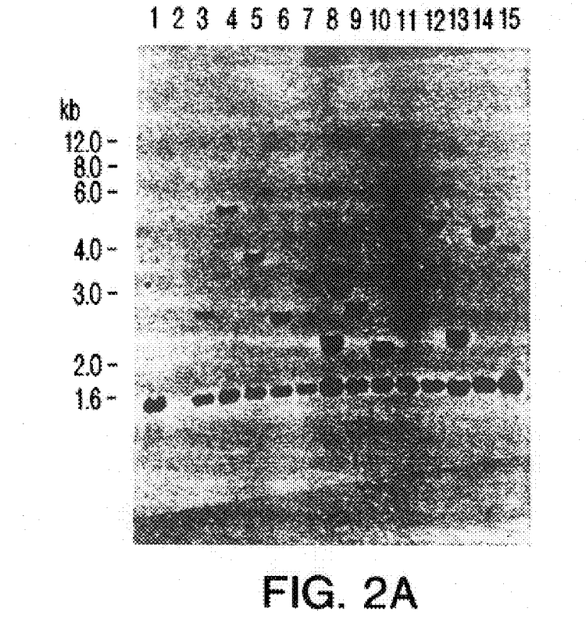
FIG. 2A shows Kan$^r$ *M. phlei* cells mutagenized with Tn5367 using phAE77 as a delivery phage. Chromosomal DNA was digested with PstI and ApaLI and hybridized with the aph gene. Lane 1 contains pYUB553 digested with PstI and ApaLI.
Figure 2B:
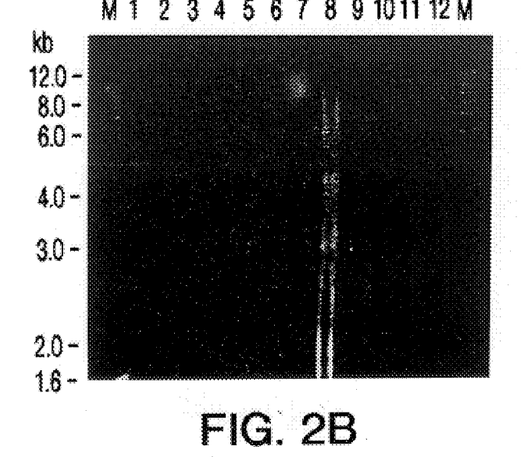
FIG. 2B shows an ethidium-bromide stained agarose gel of chromosomal DNAs of various *M. smegmatis* strains (lanes 2 to 10); *M. phlei* (lane 11) and *M. vaccae* (lane 12) were digested with ApaLI.
Figure 2C:
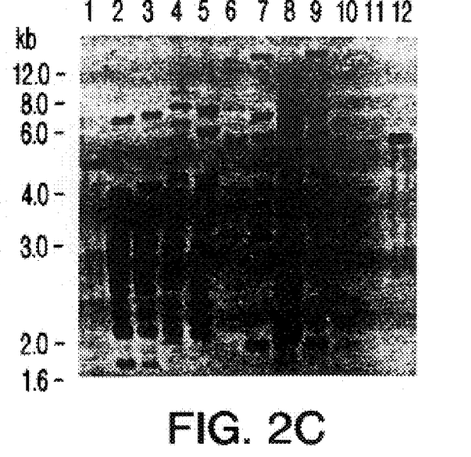

In subsequent experiments infecting mc$^2$19 cells with phAE94 at MOI of 1, greater than 2000 Kan$^R$ has been routinely obtained. Southern analysis revealed that the transposition occurred in a random fashion in *M. phlei* (FIG. 2A) and in the three *M. smegmatis* strains (data not shown). The inability to observe transpositions in some strains such as *M. fortuitum* or *M. chelonei* is likely a result of the inability of the phages to infect these strains. The ability of phAE94 to form plaques on the fast-growing strains at permissive temperature was shared by all the strains that yielded transpositions, but was not sufficient to predict the transposition efficiency. Nor was the number of copies of IS1096 predictive of transposition efficiency, as an *M. smegmatis* strain with 11 copies yielded as many transpositions as one strain with two, or *M. phlei* that had none (FIGS. 2B and 2C). Interestingly, the presence of IS1096 appears to be uniquely diagnostic for *M. smegmatis* strains as all eight strains that had the insertion sequence (FIGS. 2B and 2C) yielded a common restriction fragment length polymorphism following PCR amplification of the hsp60 gene product (Telenti, A., et al. (1973) *J. Clin. Microbiol.* 31, 175–178, (data not shown)).

Delivery of transposons in slow-growing mycobacteria using conditionally-replicating shuttle phasmids. For slow-growing mycobacteria, the expression time required for optimal transposition following phage infection was unknown. Therefore, the effect of time of incubation was tested with the phage prior to plating on kanamycin-containing media. Maximal number kanamycin-resistant colonies were obtained after 4 h of incubation of *M. tuberculosis* using phAE94 (see Table 2).

TABLE 2

Effect of Incubation Time on Transpositions in BCG and M. tuberculosis

| Strain | Time of adsorption Hours | Kan$^r$ colonies/10$^9$ input cells phAE94 |
|---|---|---|
| BCG | 0.5 | 0 |
| BCG | 2.0 | 0 |
| BCG | 4.0 | 0 |
| BCG | 6.0 | $2 \times 10^{-8}$ |
| BCG | 8.0 | $1 \times 10^{-8}$ |
| M. tuberculosis | 6.0 | $1.7 \times 10^{-7}$ |
| M. tuberculosis | 6.0 | $3.5 \times 10^{-7}$ |
| M. tuberculosis | 6.0 | $8.0 \times 10^{-7}$ |

Figure 3:
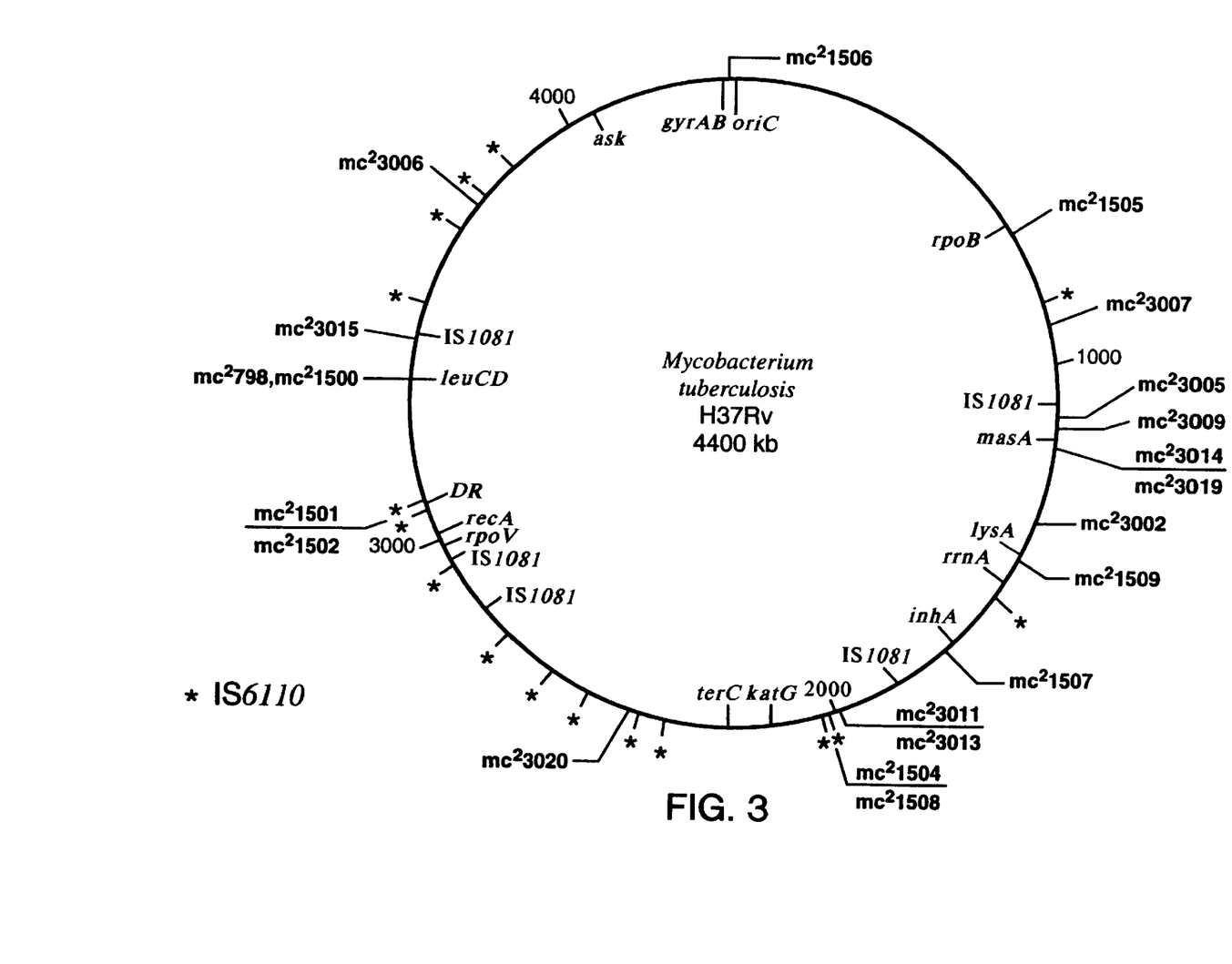

Surprisingly, phAE94 yielded none or relatively few transposon mutants in BCG. Using *M. tuberculosis* (Erdman) in three independent experiments, phAE94 yielded 1,700; 3,500; and 8,000 transposon mutants, respectively. Southern analyses of chromosomal DNA from 20 randomly picked Kan$^r$ colonies of either BCG or *M. tuberculosis* revealed a random distribution of the transposon insertions (data not shown). To further characterize the distribution of the Tn5367 insertions, the DNA sequences adjacent to the transposon insertions were determined for 11 Kan$^r$ clones of BCG and 13 clones of *M. tuberculosis* (see Table 3, below). All 24 transposon insertions analyzed were accompanied by an 8 bp target duplication, as was described previously for 9 other Tn5367 insertions (McAdam, R. A., et al. (1995) *Infect. Immun.* 63 1004–1012). The total of 33 insertions are all within different target sites, demonstrating that Tn5367 transposes with little or no sequence specificity. The chromosomal DNA sequence into which Tn5367 had inserted could be readily identified as they revealed 100% identity on a DNA level with reported cosmid sequences (Phillippe, W. J., et al. (1996) *Proc. Natl. Acad. Sci. USA* 93, 3132–3137). The inactivated genes could be predicted following a BLAST analysis compared to NCBI database (Table 3). Notably, the leuD auxotroph mc$^2$1500 isolated in BCG resulted from Tn5367 insertion in the sixth codon of the leuD gene. This insertion site is different from mc$^2$797 leuD and mc$^2$798 leuD transposon mutants reported previously (McAdam, R. A., et a. (1995) *Infect. Immun.* 63, 1004–1012). In two *M tuberculosis* mutants, mc$^2$3014 and mc$^2$3019, two independent Tn5367 insertions at widely separated regions of a large gene that has homology to polyketide sinthase gene were identified. The insertions in BCG and *M. tuberculosis* (Erdman) have been positioned on the *M. tuberculosis* H37Rv physical map (Phillippe, W. J., et al. (1996) *Proc. Natl. Acad. Sci. USA* 93, 3132–3137) and it is shown that the insertions are scattered within every quadrant of the genome (see FIG. 3).

TABLE 3

Mapping of Tn5367 insertion mutants in M. tuberculosis and BCG.

| Mutant | Gene Interrupted | SC or MC Cosmid | Sequence |
|---|---|---|---|
| M. tuberculosis | | | |
| mc$^2$3002 | unknown | cY75.unf (SC) | CATTCATT |
| mc$^2$3003 | Ferritin H (rsgA) | MTCY1A6 (SC) | AATAAACC |
| mc$^2$3004 | unknown | cY23H3 (SC) | CGTTATCG |
| mc$^2$3005 | unknown | cSCY03A11 (SC) | TGTTTGAC |
| mc$^2$3006 | Transketolase | cY454 (SC) | GTGAAACC |
| mc$^2$3007 | unknown | MTCY31 (SC) | GCTTTTAC |
| mc$^2$3008 | Acetyl-CoA synthetase in MAS operon | MSGY409(MS) | GGTTTTGA |
| mc$^2$3011 | unknown | cY28.unf (SC) | GGTTTCCC |
| mc$^2$3014 | Polyketide synthase | cSCY22G10 (SC) | CAGTAACG |
| mc$^2$3015 | Thiosulfate sulfur transferase | cY164 (SC) | GGTGATCC |
| mc$^2$3017 | Imidazole glycerol phosphate dehydratase | not found | GTGATACA |
| mc$^2$3019 | Polyketide synthase | Y275.unf (SC) | CGGTTTGC |
| mc$^2$3020 | Alcohol dehydrogenase (C-terminus) | MTCY190 (SC) | TGGAAACC |
| BCG | | | |
| mc$^2$1500 | leuD (insertion in the 6$^{th}$ codon) | not found | GTGAAAGG |
| mc$^2$1501 | DR | cSCY16B7 (SC) | CCAAAACC |
| mc$^2$1502 | DR | cSCY16B7 (SC) | CAAAACCC |
| mc$^2$1503 | unknown | not found | CAAAACCC |
| mc$^2$1504 | unknown | cY28.unf (SC) | TTCAAACT |
| mc$^2$1505 | Translation elongation factor G (efg) | not found | GTTTTTCG |
| mc$^2$1506 | 8-Amino-7-oxononaate synthase(bioF) | MTCY10H4(SC) | |

III. Discussion

To facilitate transposon-mediated insertional mutagenesis in pathogenic mycobacteria, conditionally-replicating shuttle phasmids are herein described that efficiently deliver transposons to both fast-growing *M. smegmatis* and *M. phlei* species, and the slow-growing species BCG and *M. tuberculosis*. While in the fast growing mycobacteria transposon mutagenesis has been achieved using non-replicating plasmids (Martin, C., et al. (1990) *Nature* (London) 21, 739–743; Fomukong, N. G., et al. (1993) *Gene* 130, 99–105; England, P. M., (1991) *Mol. Microbiol.* 5, 2047–2052; McAdam, R. A., et a. (1995) *Infect. Immun.* 63, 1004–1012), phage delivery offers significant advantages for transposon mutagenesis of BCG and *M. tuberculosis*. The non-replicating plasmids are of limited use in slow growing mycobacteria, because of the low transformation frequencies obtained with electroporation. The disadvantage of the conditionally replicating plasmid system is that unless the transposition event is regulated, there is no means to select against propagation of transposon mutants during the outgrowth stage, with the consequence that many of the mutants selected will be siblings of a few mutated cells. In contrast, with a conditionally-replicating phage system where essentially every cell is infected, the selection can be executed shortly after infection, and the mutations are likely to represent independent events. Analysis of the BCG and *M. tuberculosis* independent mutants set forth herein suggests this to be the case.

The transposon Tn5367 used for insertional mutagenesis has several particularly desirable features. As shown previously (McAdam, R. A., (1995) *Infect. Inmmun.* 63, 1004–1012) and confirmed herein, Tn5367 transposes in a relatively random fashion and therefore allows for insertions in virtually every gene of a mycobacterial genome. Transposition frequencies could be improved by fusing the transposase to more active promoters or expression signals, and additionally provide transposon elements (mini-Tn5367) that can no longer transpose once dissociated from their transposase. Transposon containing promoter-less reporter genes could be engineered that would allow for the generation of libraries that permit the screening of regulated promoters, as has been done in other genera (Kleckner, et al., (1991) *Meth. Enzymol.* 204, 139–180).

In addition to delivering useful transposon constructs, the conditionally-replicating shuttle phasmids represent potentially versatile vectors for genetic transfer. At present, an additional 4 kb of DNA can be introduced into the pYUB552 backbone and still maintain the ability of the shuttle phasmids to yield functional mycobacteriophage. In addition to delivering transposons and creating marked insertional mutations, these vectors could be used to deliver any gene(s) to *M. tuberculosis* in a transient fashion. Infection of *M. tuberculosis* with conditionally-replicating TM4 shuttle phasmid containing the firefly luciferase gene has already increased the sensitivity of the luciferase phage reporter assay (Carriere, C. et al. (unpublished results)). Infection at the non-permissive temperature has been found both to increase the cumulative light emission, and extend the time available for the assay, as the phage is unable to proceed to lytic growth (Telenti, A., (1973) *J. Clinical Microbiol.* 31, 175–178). Transient delivery of genes encoding γδ-resolvase or Cre recombinase to *M. tuberculosis* offer unique possibilities for precise gene deletions and removal of antibiotic selective markers, that will be valuable in the creation of non-reverting, attenuated vaccine strains acceptable for use in humans. These phages may allow the development of specialized transducing phages that will efficiently mediate allelic exchanges in *M. tuberculosis*.

The ability to generate libraries of transposon mutants in *M. tuberculosis* together with the complete genomic sequence shortly to become available, provides an unprecedented opportunity to make rapid and substantial progress in the understanding of pathogenesis and development of novel therapeutics for tuberculosis. The rapid determination of sequences adjacent to the transposon insertion allows for an immediate classification of a gene as being non-essential for the multiplication of the tubercle bacillus. The set of essential genes would represent attractive candidates for analysis as practical drug targets. Many non-essential genes may represent important virulence determinants, as well. Indeed, among the mutants analyzed so far, it will be of immediate interest to examine the insertions in mycocerosic acid biosynthesic gene (Azad, A. K., Sirakova, T. D., Rogers, L. M., & Kollattukudy, P. E. (1966) *Proc. Natl. Acad. Sci. USA* 93, 4787–4792) and polyketide-biosynthetic gene [which shares significant homology to 6 of the 14 modules of the immunosuppressant rapamycin biosynthetic gene (Schwecke, T., et al. (1995) *Proc. Natl. Acad. Sci.* 92, 7839–7843.] for their possible roles in virulence of *M. tuberculosis*. Mutational analyses represent the most powerful approach available to dissect the steps and functions governing the pathogenic process of *M. tuberculosis*, thus the conditionally replicating shuttle phasmids described herein are a valuable tool in facilitating that analysis.

Although the invention herein has been described with reference to particular embodiments, it is to be understood that these embodiments are merely illustrative of various aspects of the invention. Thus it is to be understood that numerous modifications may be made in the illustrative embodiments and other arrangements may be devised without departing from the spirit and scope of the invention in the appended claims.

What is claimed:

1. A conditional shuttle phasmid comprising a TM4 mycobacteriophage which contains an *E. coli* bacteriophage lambda cosmid inserted into a non-essential region of said TM4 mycobacteriophage genome, and a transposon inserted into said *E. coli* bacteriophage lambda cosmid.

2. The conditional shuttle phasmid of claim 1, deposited under ATCC under Accession No. 209306 and designated phAE87.

3. The conditional shuttle phasmid of claim 1, wherein said transposon is Tn5367.

4. The conditional shuttle phasmid of claim 1 deposited under ATCC under Accession No. 209307 and designated phAE94.

5. The conditional shuttle phasmid of claim 1, wherein said transposon is mini-Tn10(kan).

6. A recombinant mycobacterium which expresses DNA of interest introduced into its chromosome by a conditional shuttle phasmid of claim 1.

7. The recombinant mycobacterium of claim 6 which is *M. tuberculosis, M. bovis, M. phlei* or BCG.

8. A method for producing a mutant mycobacterium comprising infecting said mycobacterium with the conditional shuttle phasmid of claim 1 wherein the infection takes place under conditions wherein said conditional shuttle phasmid does not replicate and said transposon contained in said conditional shuttle phasmid incorporates into a chromosome of said mycobacterium, thereby generating one or more mutations in said mycobacterium.

9. The method of claim 8, wherein said conditions comprise a temperature of 37° C.

10. The method of claim 8, wherein said mycobacterium is *M. tuberculosis, M. bovis, M. phlei,* or BCG.

* * * * *